United States Patent [19]
Ojakaar

[11] 3,987,033
[45] Oct. 19, 1976

[54] BLOCKED ISOCYANATES
[75] Inventor: Leo Ojakaar, Hockessin, Del.
[73] Assignee: E. I. Du Pont de Nemours and Company, Wilmington, Del.
[22] Filed: Dec. 12, 1974
[21] Appl. No.: 532,241

[52] U.S. Cl. .................... 260/239.3 R; 260/293.77; 260/471 C; 428/480
[51] Int. Cl.² ............... C07D 223/10; C07D 211/76
[58] Field of Search ................ 260/239.3 R, 293.77

[56] References Cited
UNITED STATES PATENTS
3,454,621  7/1969  Engel ........................... 260/239.3 R
3,738,981  6/1973  Graff et al .................... 260/239.3 R FOREIGN PATENTS OR APPLICATIONS
701,711  12/1953  United Kingdom ............. 260/239.3
891,009   3/1972  United Kingdom ............. 260/471 C Primary Examiner—Henry R. Jiles
Assistant Examiner—Robert T. Bond

[57] ABSTRACT

Mixtures of compounds having the formula

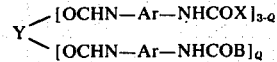

where Y is an alkyl triprimary oxy radical, Ar is a divalent radical containing an aromatic nucleus, X is aryloxy or alkoxy, B is dialkylamino or lactam-N-yl, Q is 0, 1, 2 or 3, which may be dissolved in compatible solvents and mixed with suitable catalysts and used as a coating material on organic polymers such as polyester to enhance adhesion between the substrate and a subsequently applied organic polymer such as an elastomeric polymer.

9 Claims, No Drawings

BLOCKED ISOCYANATES

BACKGROUND OF THE INVENTION

This invention relates to a composition which is a mixture of compounds useful in the preparation of a coating on polymeric substrates in order to enhance adhesion between the substrate and a subsequently applied polymeric coating. The composition is specifically useful to coat polyester yarn or cord so that it will bond better to the subsequently applied elastomeric compound.

In the elastomer reinforcing art, adhesives are used for bonding both polyester and nylon to elastomer. A coating composition is applied and cured by heating usually as part of a hot stretching operation. A conventional coating composition is an aqueous solution of Resorcinol-Formaldehyde and a Latex of a copolymer of butadiene, styrene and a vinyl pyridiene known as "RFL" adhesive.

In polyester cord reinforcement of elastomers, the art has developed the further refinement of first coating the substrate polyester with a subcoat. An organic solvent solution of a diisocyanate or a triisocyanate has been used as a subcoat, which is later coated with the "RFL" adhesive—U.S. Pat. No. 2,990,313 to Knowles. Also see U.S. Pat. No. 2,994,671 which shows phenol "blocked" isocyanates used in this manner; and U.S. Pat. No. 3,179,547 to Kigane et al. which shows ethylene imine blocked isocyanates used in this manner. Currently available in the market is toluene 2,4-diisocyanate, that has been reacted with trimethylol propane at the para position and "blocked" with phenol at the ortho position. This compound is recommended for use in subcoating polyester yarn and cord to be subsequently treated with RFL adhesive and then used to reinforce elastomers.

THE INVENTION

The present invention provides a further refinement in preparing polyester cord for reinforcement in elastomers. A composition has been found that may be used as a subcoat for polyesters that further increases the adhesion of the elastomer to the polyester. This new composition is a mixture of compounds having the formula:

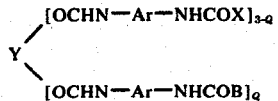

where Y is an alkyl triprimary oxy radical, Ar is a divalent radical containing at least one aromatic nucleus, X is a radical selected from the class consisting of aryloxy and alkoxy, B is a radical selected from the class consisting of dialkylamino and lactam-N-yl, Q is 0, 1, 2 or 3, the total number of X radicals in the mixture is at least equal to the number of B radicals in the mixture and the total number of B radicals in the mixture is at least 10% of the sum of the B and X radicals.

This composition may be prepared by reacting an aromatic diisocyanate with a triprimary alcohol, and subsequently reacting this product with a mixture of a hydroxy component such as a phenol and an amine type material such as a lactam. This composition may also be prepared by reacting the hydroxy component with one batch of triprimary alcohol-diisocyanate adduct and reacting another batch with an amine type material and then blending the batches.

The triprimary alcohol used to react with the diisocyanate may contain from 4 to 15 carbon atoms, representative alcohols are trimethylol methane, 1,1,1 trimethylol propane, 1,1,1 trimethylol dodecane, and 1,2,3 trimethylol butane. When 1,1,1 trimethylol propane is used as a reactant, the Y radical is propylidyne-trimethoxy.

The aromatic diisocyanate may contain only a single aromatic nucleus, like toluene 2,4 diisocyanate, or it may contain more than one aromatic nucleus like methylene-bis (4-phenylisocyanate). Other representative diisocyanates that may be used are 2,6-tolylene diisocyanate, 1,3-phenylene diisocyanate, and mixtures of these compounds. Other diisocyanates well known in the art can also be employed. When a toluene diisocyanate is used as a reactant the Ar radical is methylphenylene.

The hydroxyl compound that is reacted with the isocyanate group can be a aromatic alcohol, a high molecular weight aliphatic alcohol, 10–18 carbon atoms, or a heterocyclic alcohol such as furfuryl alcohol. Aromatic alcohols are preferred, and aromatic alcohols having at least one aliphatic side chain having 1 to 12 carbon atoms are the most preferred. Mixtures of hydroxyl compounds may also be employed. A satisfactory mixture that is commercially available contains both ortho and para branched chain nonylphenol and about 5% by weight 2,4-dinonylphenol. Other specific hydroxy compounds that are representative are phenol, 4-octylphenol, β-naphthol, and dodecyl alcohol. In general, the hydroxy compound will be selected on the basis of the unblocking temperature that is desired in the isocyanate, and on the basis of the volatility of the hydroxy compound. Usually it is desirable that the isocyanate unblock at a temperature below 450° F. and that the hydroxy compound have a low volatility. When nonyl phenol is used as a reactant the X radical is nonylphenoxy.

The amine type material that is reacted with the isocyanate group can be a lactam, such as ε-caprolactam or γ-valerolactam, or an aliphatic secondary amine such as diisopropyl amine, di-n-butyl amine. Mixtures of amine compounds can also be employed. When ε-caprolactam is used as a reactant, the B radical is caprolactam-N-yl.

The reaction between the triprimary alcohol and the aromatic diisocyanate is usually carried out in a solution. Suitable solvents for the compounds include ethyl acetate, butyl acetate, trichloroethylene, and polyethylene glycol dioctoate having a molecular weight corresponding to 3 to 7 oxyethylene units. The triol and the aromatic diisocyanate are added to the reactor kettle in the mole ratio of 1 mole of triol to 3 moles of diisocyanate. The reaction is carried out in the presence of a suitable amount of a conventional catalyst such as dimethylcyclohexylamine. The reaction temperature may be controlled within the limits of about 70°–90° C. by the addition of solvent or by conventional heating-cooling devices—i.e. coils, etc. Upon completion of this reaction, the hydroxy compound and the amine type compound are added to the reactor kettle in the mole ratio desired in the final product and the blocking reaction is carried to completion.

The product is then ready for use as a coating for the polymer substrate. Subcoatings of this type are applied in many different methods in the art, but may be applied by merely dipping the yarn in the solution of the product. Solutions of about 40% by weight of the compositions of this invention have the additional desirable property of low viscosity at 25° C., and thus can be applied to the yarn at room temperature. In order to achieve maximum adhesive properties in the final elastomeric product, it is usually desirable to provide a suitable catalyst in the subcoating composition. An especially desirable catalyst for use with compositions of this invention is 2,4,6-tri(dimethyl amino methyl) phenol. Another satisfactory catalyst is 1,4-diazabicyclo[2.2.2.]octane, which has the formula $N(CH_2CH_2)_3N$. The amount of coating on the substrate will usually be in the range of about 0.2 to about 5% by weight of the substrate. The coated substrate is then ready for the application of the RFL coating in the conventional manner.

EXAMPLE 1

A kettle fitted with a stirrer, a reflux condenser, inlet lines for nitrogen and starting materials, and an outlet for the product is dried and flushed with nitrogen. The kettle is also fitted with a heating-cooling system and a temperature sensing device. Into the kettle are charged 18.06 lb. toluene 2,4-diisocyanate, 15.0 lb. of a commercially available polyethylene glycol dioctoate having a molecular weight corresponding to 3 to 7 oxyethylene units, and 0.1 lb. dimethylcyclohexylamine catalyst. A solution of 4.64 lb. trimethylolpropane in 20.0 lb. of polyethylene glycol dioctoate was added at such a rate as to hold the reaction mass at 80° C. After the reaction was complete (checked by -NCO level) 0.1 lb. dimethylcyclohexylamine catalyst was added. While holding the temperature at 80°–90° C. a solution of 11.42 lb. 4-nonylphenol and 5.88 lb. ε-caprolactam in 15.0 lb. of polyethylene glycol dioctoate was rapidly added. Heating was continued until the level of -NCO dropped to 0. To the reaction mass was then added a solution of 1.8 lb. 4,4'-thio-bis(6-butyl-2-methylphenol) to stabilize the polyethylene glycol dioctoate.

EXAMPLE 2

The procedure of Example 1 was repeated twice substituting 5.24 lb. diisopropyl amine and 11.42 lb. 4-nonylphenol, and 5.88 lb. ε-caprolactam and 7.55 lb. β-naphthol for the ε-caprolactam and 4-nonylphenol.

EXAMPLE 3

The proportions of 4-nonylphenol and ε-caprolactam (or their substitutes) may be varied in Example 1, as may be the identity of the blocking agents (shown in Example 2) or the triol.

Blocked isocyanates made according to the process of Example 1 and other blocked isocyanates made by substitution of ingredients in the procedure outlined in Example 1 were coated on a commercially available polyethylene terephthalate yarn of 100 denier by passing the yarn through a slot applicator through which a 40% solution maintained at about 25° C. of the blocked isocyanate in polyethylene glycol dioctylate, having a molecular weight corresponding to 3 to 7 ethylene glycol units, was pumped. The coated yarn was then coated in accordance with usual procedures with "RFL" adhesive and subsequently cured.

In Table I the testing results are shown for samples cured at temperatures of 455° F. and 475° F. In Table I the adduct employed was trimethylolpropane-toluene diisocyanate. The coating also contained 1 weight % 2,4,6-tri(dimethyl amino methyl)phenol catalyst. The hot 2 ply adhesion test referred to in the table is ASTM test D-2138. The Disc Fatigue Test employed is set forth in Tim-Yam Au's U.S. Pat. No. 3,090,997 at column 4, lines 51–53. The Disc Fatigue Test was run at 11.5% compression and 7.2% extension.

TABLE I

| | | | 455° F. Cure | | 475° F. Cure | |
|---|---|---|---|---|---|---|
| Specimen | Blocking Agents (Equal molar quantities of each) | Coating Solution Viscosity (25° C) | Hot 2 Ply Adhesion | Disc Fatigue Break Strength Loss | Hot 2 Ply Adhesion | Disc Fatigue Break Strength Loss |
| 1 | α-caprolactam 4-nonylphenol | 38 csp | 38 lb. | 18% | 40 lb. | 30% |
| 2 | α-caprolactam furfuryl alcohol | 31 csp | — | — | 32 lb. | 13% |
| 3 | diisopropylamine 4-nonylphenol | 138 csp | 35 lb. | 19% | 30 lb. | — |
| 4 | diisopropylamine furfuryl alcohol | 32 csp | 28 lb. | 12% | 31 lb. | 13% |

The effect of the addition of various amounts of the catalyst, 2,4,6-tri(dimethyl amino methyl)phenol, to the equal molar ε-caprolactam/4-nonylphenol blocked adduct of trimethylolpropane and toluene diisocyanate on adhesion when cured at various temperatures is illustrated by the results shown in Table II. The yarn was coated and treated as specified with regard to the yarns used in Table I.

TABLE II

| | Curing Temperatures | | |
|---|---|---|---|
| | 425° F. | 455° F. | 470° F. |
| % by weight catalyst | Hot two ply adhesion | | |
| 0 | 19 lb. | 26 | 28 |
| 0.5 | 18 | 27 | 33 |
| 1.0 | 27 | 30 | 36 |
| 2.0 | 30 | 34 | 36 |

I claim:
1. A composition comprising a mixture of compounds having the formula

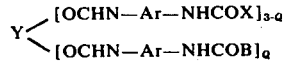

where Y is an alkyl triprimary oxy radical having 4 to 15 carbon atoms formed by the reaction of a triprimary alcohol selected from the class consisting of trimethylol methane, 1,1,1 trimethylol propane, 1,1,1 trimethylol dodecane, and 1,2,3 trimethylol butane and an isocyanate group, Ar is a divalent radical containing at least one aromatic nucleus, and is selected from the class consisting of phenyl, methyl phenylene, and methylene-bis-phenyl, X is a radical selected from the class consisting of aryloxy having an aliphatic side chain of 1 to 12 carbon atoms and alkoxy having 10 to 18 carbon atoms, B is lactam-N-yl, Q is 0, 1, 2, or 3, the total number of X radicals in said mixture being at least equal to the total number of B radicals in said mixture, and the total number of B radicals in said mixture is at least 10% of the sum of the B and X radicals.

2. The composition of claim 1 in which Y contains 4-15 carbon atoms.

3. The composition of claim 2 in which X is aryloxy having at least one alkyl side chain of 1-12 carbon atoms.

4. The composition of claim 3 in which the alkyl side chain contains nine carbon atoms.

5. The composition of claim 2 in which B is a lactam-N-yl radical having 6 to 12 carbon atoms.

6. The composition of claim 1 dissolved in a compatible solvent selected from the class consisting of ethyl acetate, butyl acetate, trichloroethylene, and polyethylene glycol dioctoate having a molecular weight corresponding to 3 to 7 oxyethylene units.

7. The composition of claim 6 containing 1 to 2% by weight based on the amount of the mixture of compounds of claim 1 of 2,4,6-tri(dimethyl amino methyl) phenol.

8. The composition of claim 6 in which the solvent is polyethylene glycoldioctoate.

9. The composition of claim 1 in which Y is propylidynetrimethoxy, Ar is methylphenylene, X is the radical nonylphenoxy, and B is caprolactam-N-yl.

* * * * *